(12) United States Patent
Ebinuma

(10) Patent No.: US 7,329,520 B2
(45) Date of Patent: Feb. 12, 2008

(54) FRUCTOSYL PEPTIDE OXIDASE AND UTILIZATION THEREOF

(75) Inventor: Hiroyuki Ebinuma, Ibaraki (JP)

(73) Assignee: Daiichi Pure Chemicals Co., Ltd., Tokyo (JP)

( * ) Notice: Subject to any disclaimer, the term of this patent is extended or adjusted under 35 U.S.C. 154(b) by 316 days.

(21) Appl. No.: 10/531,305

(22) PCT Filed: Oct. 23, 2003

(86) PCT No.: PCT/JP03/13548

§ 371 (c)(1),
(2), (4) Date: Apr. 13, 2005

(87) PCT Pub. No.: WO2004/038034

PCT Pub. Date: May 6, 2004

(65) Prior Publication Data

US 2007/0054344 A1    Mar. 8, 2007

(30) Foreign Application Priority Data

Oct. 23, 2002    (JP) .............................. 2002-308731

(51) Int. Cl.
*C12P 21/06*    (2006.01)
*C12N 9/24*    (2006.01)
*C12N 9/06*    (2006.01)

(52) U.S. Cl. ...................... 435/191; 435/200; 435/68.1

(58) Field of Classification Search ...................... None
See application file for complete search history.

(56) References Cited

U.S. PATENT DOCUMENTS

2006/0172367 A1*    8/2006    Yoshida et al. ................ 435/27

FOREIGN PATENT DOCUMENTS

| EP | 1 223 224 A1 | 7/2002 |
|---|---|---|
| JP | 5-192193 | 8/1993 |
| JP | 6-46846 | 2/1994 |
| JP | 7-289253 | 11/1995 |
| JP | 8-154672 | 6/1996 |
| JP | 8-336386 | 12/1996 |
| JP | 11-155579 | 6/1999 |
| JP | 2000-333696 | 12/2000 |
| JP | 2001-54398 | 2/2001 |
| JP | 2001-095598 | 4/2001 |
| JP | 2001-95598 | 4/2001 |
| WO | 97/13872 | 4/1997 |
| WO | 02/06519 | 1/2002 |
| WO | WO 02/44387 A1 | 6/2002 |

OTHER PUBLICATIONS

Univeristy of Hawaii botany database "Zingiberaceae", webpage printed Jul. 30, 2007, http://www.botany.hawaii.edu/faculty/carr/zingiber.htm.*
Wu (2003) Arch. Biochem. Biophys. 419(1): 16-24.*
Wu et al. (2001) Biochemistry 40(43): 12886-95.*
Kobold, Uwe et al. "Candidate reference methods for hemoglobin A1c based on peptide mapping", Clinical Chemistry, vol. 43, No. 10, pp. 1944-1951 1997.
U.S. Appl. No. 10/531,321, filed Apr. 14, 2005, Ebinuma.
U.S. Appl. No. 10/531,305, filed Apr. 13, 2005, Ebinuma.
Nobuyuki Yoshida, et al., "Distribution and Properties of Fructosyl Amino Acid Oxidase in Fungi", Applied and Enviromental Microbiology, vol. 61, No. 12, XP-000561863, Dec. 1, 1995, pp. 4487-4489.

* cited by examiner

*Primary Examiner*—Lisa J Hobbs
(74) *Attorney, Agent, or Firm*—Oblon, Spivak, McClelland, Maier & Neustadt, P.C.

(57) ABSTRACT

The present invention is directed to a defructosylation enzyme originating from a plant, a method of defructosylating a fructosylated peptide or protein through use of the enzyme, and a method of measuring a fructosylated peptide or protein.

7 Claims, 4 Drawing Sheets

FRUCTOSYL PEPTIDE OXIDASE AND UTILIZATION THEREOF

TECHNICAL FIELD

The present invention relates to a method of defructosylating a fructosylated peptide or a fructosylated protein through use of an enzyme, to a novel enzyme having defructosylating ability, and to a method of assaying a fructosylated peptide or a fructosylated protein through measuring a reaction product obtained from the defructosylation method.

BACKGROUND ART

Hemoglobin (Hb) A1c is a stable Amadori product formed through Amadori rearrangement of a Schiff base which is nonenzymatically produced between the amino group of β-chain N-terminus valine and the aldehyde group of glucose. It is also classified as a glycated protein having a structure formed of a valine residue and fructose bonded thereto. Clinically, HbA1c is correlated with a mean blood sugar level of past one to two months, and therefore, HbA1c serves as an important indicator in control of diabetes. Thus, there still exists demand for a quantitative HbA1c assay method which is rapid, convenient, accurate, and practical.

As a practical standard assay methodology for HbA1c, IFCC (International Federation of Clinical Chemistry and Laboratory Medicine) adopts a method which includes separation, by HPLC, of a β-N-terminal 6-peptide fragment which is likely to have fructosyl valine and is obtained through hydrolysis of hemoglobin with endoprotease Glu-C and quantitation of the separated fragment through capillary electrophoresis or mass spectrometry (Kobold U., et al; Candidate Reference Methods for Hemoglobin A1c Based on Peptide Mapping; Clin. Chem., 43, 1944-1951 (1997)). However, this method requires a special apparatus and entails cumbersome maneuvers and poor economy, making this method impractical.

Existing methods for measuring HbA1c which are currently employed in practice include HPLC employing, as a carrier, a special hard gel having a hydrophobic group or a cation exchange group, and latex immunoagglutination employing anti-HbA1c antibody. These existing methods, requiring expensive instruments or multi-step immunological reactions, are not necessarily satisfactory in terms of speed, convenience, or accuracy.

In recent years, there have been reported enzyme-based assay method for glycated proteins, such as HbA1c and glycated albumin, which include degradation of glycated protein with protease, and employment of fructosyl amino acid oxidase (FAOD) or a similar enzyme that reacts on a glycated amino acid (Japanese Patent Application Laid-Open (kokai) Nos. H05-192193, H07-289253, H08-154672, H06-046846, and H08-336386, WO97/13872, WO02/06519, Japanese Patent Application Laid-Open (kokai) No. 2001-054398).

In any of these methods, in order to avoid difficulty encountered by FAOD or a similar enzyme in acting on glycated protein, regardless of the glycated protein being HbA1c or glycated albumin, glycated amino acids (fructosyl valine for HbA1c; fructosyl lysine for glycated albumin) which are characteristic to respective glycated proteins are cut out from a glycated peptide or glycated protein, and the obtained glycated amino acids are used as substrates for FAOD, etc. Therefore, glycated amino acids for such purposes have to be cut out effectively so that they can serve as substrate for FAOD, etc.

To achieve the above object, research efforts have been undertaken to search for a protease which enables glycated amino acids to be effectively cut out from glycated protein, and heretofore, numerous proteases have been reported. However, no report has disclosed information about the method of cutting out the glycated amino acid (or a peptide containing the glycated amino acid) from a glycated protein, or, in more specifically, the length of the peptide chain cut out from the glycated protein. From this viewpoint, therefore, it remains unknown as to whether or not the disclosures of the above publications are in fact practical.

Meanwhile, Japanese Patent Application Laid-Open (kokai) No. 2001-95598 discloses a method for measuring glycated protein, in which a sample is treated with protease, and the resultant free-form glycated peptide is reacted with glycated peptide oxidase. In the disclosed method, however, there still remains an unsolved problem in that, since the glycated peptide oxidase substantially acts on fructosyl dipeptide, the method is not effective for a fructosyl peptide, which is longer than fructosyl dipeptide, and similar to the case of the conventional approach of using FAOD or a similar substance, a fructosyl dipeptide capable of serving as a substrate must be cut out effectively.

In another report, FAOD is used in combination with another enzyme (Japanese Patent Application Laid-Open (kokai) No. 2000-333696). However, the disclosed method is directed to improvement in measurement sensitivity by measuring hydrogen peroxide from two different sources; i.e., hydrogen peroxide generated from reaction between FAOD and glycated amino acid cut out with protease, and the other hydrogen peroxide generated from reaction between glucosone, which is a concurrently generated degradation product of glycated amino acid, and glucose oxidase. Thus, the method does not intend to perform defructosylation of glycated peptides of different lengths.

DISCLOSURE OF THE INVENTION

Accordingly, an object of the present invention is to provide an enzyme exhibiting defructosylation action on HbA1c or other fructosylated proteins, or fructosylated peptides of different sizes obtained through cutting such fructosylated proteins; a method of defructosylation by use of the enzyme; and a method of measuring fructosylated peptide or protein making use of a defructosylation reaction.

The present inventors have devoted efforts to attain the above object by searching for a useful enzyme in the natural world, and as a result, have found that, as contrasted to the fact that existing enzymes, such as FAOD, which have been reported to be endowed with defructosylation action are derived from microorganisms, certain plants are sources of enzymes exhibiting defructosylation action, and that enzymes originating from such plants exhibit defructosylation action, regardless of the length of the peptide chain of a fructosyl peptide, thereby leading to completion of the invention.

Accordingly, the present invention provides a method for defructosylating a fructosylated peptide or protein, characterized by comprising reacting, with the peptide or protein, an enzyme which is extracted from a plant and exhibits defructosylation action.

The present invention also provides an enzyme having defructosylating a fructosylated peptide or protein, the enzyme being extracted from a plant.

The present invention also provides a method for measuring a fructosylated peptide or protein, characterized by comprising measuring at least one reaction product obtained through use of the above defructosylation method.

The defructosylation enzyme of the present invention enables defructosylation of N-terminal-valine fructosylated peptide or protein. Moreover, through quantitation of the resultant reaction product, a similar substance of N-terminal-valine fructosylated peptide, protein, or subunits of protein, e.g. HbA1c, can be quantitatively determined accurately.

BEST MODE FOR CARRYING OUT THE INVENTION

Figure 1:
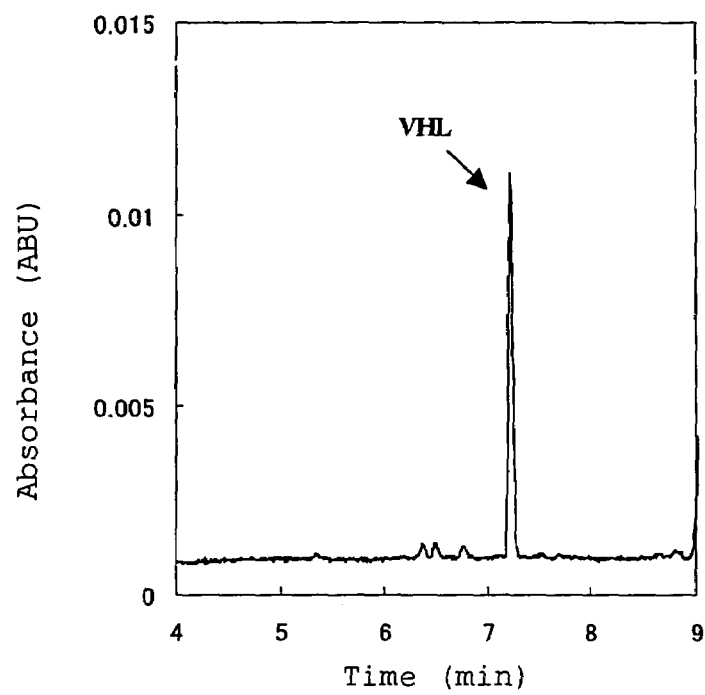
FIG. 1 shows the results of capillary electrophoresis obtained from the reaction mixture 1 prepared by reacting a Zingiberaceae-plant-origin defructosylation enzyme with fructosyl tripeptide (f-VHL).

As used herein, the term "defructosylation" refers to removing a fructosyl moiety from a fructosyl amino acid or fructosyl peptide (i.e., fructosylated amino acid or fructosylated peptide) through, for example, oxidation decomposition, thereby generating non-fructosylated amino acid or peptide.

No particular limitation is imposed on the enzyme employed in the present invention (hereinafter referred to as "defructosylation enzyme"), so long as the enzyme exhibits defructosylation action on a fructosylated peptide or protein. However, defructosylation enzymes originating from a plant are preferred, since such enzymes are capable of acting on fructosyl peptides having different lengths. The defructosylation enzyme of the present invention is preferably an enzyme which produces glucosone and a defructosylated peptide or protein from a fructosyl peptide or protein. No particular limitation is imposed on the plant containing the enzyme of the present invention. However, plants belonging to the family Zingiberaceae are particularly preferred. Examples of the plants belonging to the family Zingiberaceae include Zingiber officinale, Zingiber mioga, and Curcuma longa. No particular limitation is imposed on the portion of a plant employed for extracting the enzyme of the present invention, so long as the portion contains the defructosylation enzyme, and portions such as leaf, stem, flower, rhizome, and root may be employed. Alternatively, products of these plants such as juice produced from extracts and freeze-dried preparations may also be employed.

Extraction of the defructosylation enzyme from such a plant may be performed by directly disrupting and then squeezing the plant. Alternatively, prior to disruption and extraction, an appropriate buffer or a similar solution may be added to the plant. In the present invention, an extract as such may be employed. However, a purified extract is preferred. Purification may be performed through a known method. Specifically, there may be employed a suitable combination of any of ammonia sulfate fractionation processes and column chromatography processes such as ion-exchange chromatography, hydrophobic chromatography, hydroxyapatite gel, and gel filtration. In order to remove the effect of polyphenol contained in the plant extract, additional treatments may be performed through use of a reducing agent, absorbent polymer, or a similar agent.

An enzyme originating from a plant belonging to the family Zingiberaceae, an enzyme of the present invention, has the following physical and chemical characteristics (a) to (g):

a) Action: in the presence of oxygen, acting on a fructosyl valine or fructosyl peptide (at least on fructosyl peptides having amino acid sequences represented by SEQ ID NOs: 1 to 5) and catalyzing a reaction which produces corresponding valine or non-fructosyl peptide, glucosone, and hydrogen peroxide;
b) Optimum pH: 8.0 to 9.0;
c) Range of stable pH: pH 6.0 to 7.0;
d) Km value for fructosyl valyl histidine: 1.2 mM;
e) Optimum Temperature range: 60° C. or higher;
f) Temperature stability: at least 80% of enzyme activity remains after heat-treatment for 15 minutes at 50° C.; and
g) Molecular weight: approximately 27 kDa (gel filtration).

These characteristics indicate that the enzyme is a fructosyl peptide oxidase.

The method for determining activity of the enzyme of the present invention is exemplified by a method in which the enzyme is reacted with a substrate fructosyl peptide, to thereby produce non-fructosyl peptide, glucosone, and hydrogen peroxide, and the amount of any one of these compounds produced through the enzyme reaction is measured. Next will be described an example method of measuring the amount of glucosone produced. Hereinafter, unless otherwise specified, the substrate employed for determining activity of the enzyme of the present invention is fructosyl valyl histidine. One unit (U) of the titer of the enzyme is defined as the amount of enzyme which produces 1 μmol glucosone in one minute as measured when the substrate is fructosyl valyl histidine.

Method for Determining Activity of the Enzyme (Production of Glucosone)

200 mM Phosphate buffer (pH 8.0) (150 μL), purified water (360 μL), and 10 mM fructosyl valyl histidine (60 μL) (as a substrate) were mixed together, and the enzyme solution of the present invention (30 μL) was added thereto, followed by heating for 5 to 60 minutes at 37° C.

(Measurement of Glucosone)

To the above reaction mixture, a mixture which has been prepared in advance by mixing 200 mM acetate buffer (pH 6.0) (750 μL), 4000-u/mL glucose oxidase (Toyobo Co., Ltd.) (450 μL), 0.15% 4-aminoantipyrine (300 μL), 0.3% TOOS (Dojindo Laboratories) (300 μL), 500-u/mL peroxidase (Toyobo Co., Ltd.: Type III) (300 μL), and 1% sodium azide (300 μL) is added, followed by heating for 10 minutes at 37° C. Thereafter, absorbance is measured at 550 nm. A control system is prepared by repeating the above procedure, except that purified water is added instead of the substrate. The amount of glucosone is obtained from the amount of the dye produced. Specifically, a calibration curve is prepared by repeating the above-described procedure, except that serially diluted glucose is employed as a substrate, and purified water is employed instead of the enzyme solution of the present invention. Thus, the amount (in micromoles) of glucosone produced in one minute is calculated, and the obtained value is used as the activity unit of the enzyme solution.

The defructosylation enzyme of the present invention enables effective measurement of glycated protein, since the defructosylation enzyme of the present invention is capable of acting on fructosyl peptides of any size that are produced from glycated protein through protease decomposition, thus eliminating need to add another protease for cleaving the protein and time for the treatment. In addition, the defructosylation enzyme of the present invention finds utility not only in clinical tests, but also in various other fields, including the medical field. The defructosylation enzyme of the present invention has, similar to FAOD, decomposition action on the substrate fructosyl peptide through oxidation, to thereby defructosylate the peptide with generating hydrogen peroxide, glucosone, or other substances. Thus, the defructosylation enzyme of the present invention is particularly advantageous in that the generated hydrogen peroxide can be measured in a known measurement system through use of an enzyme such as peroxidase. No particular limitation is imposed on the fructosylated peptide or fructosylated protein to be treated through the defructosylation method of the present invention, so long as the defructosylation enzyme acts on the peptide or protein. However, HbA1c and fructosyl peptides having fructosylated valine at the N-terminus of a hemoglobin β-chain are particularly preferred. No particular limitation is imposed on the number of amino acid residues contained in the N-terminal-valine fructosylated peptide. However, fructosyl peptides having an amino acid sequence represented by any of SEQ ID NOs: 1 to 5 are particularly preferred.

The above-described N-terminal-valine fructosylated peptide may be prepared by treating a peptide or protein having any of the above-mentioned sequences such as HbA1c with, for example, a suitable endoprotease or exoprotease. Examples of the protease include elastase, proteinase K, pepsin, alkaline protease, trypsin, proline-specific endoprotease, V8 protease, carboxypeptidase A, and carboxypeptidase B. The protease used to prepare the fructosyl peptide preferably exhibits an activity of 0.05 to 10,000 U/mL, particularly preferably 10 to 2,000 U/mL.

Among a variety of conditions under which the defructosylation enzyme of the present invention originating from a plant belonging to the family Zingiberaceae is reacted with a fructosylated peptide or protein, the treatment temperature is preferably 20 to 60° C., more preferably 30 to 50° C., and the treatment time is preferably 3 minutes to 100 hours, more preferably 5 minutes to 20 hours. Through the treatment, reaction products containing hydrogen peroxide, glucosone, and defructosyl peptides can be obtained. Therefore, through measuring one or more of the reaction products, fructosylated peptide or protein can be measured.

In order to determine the enzyme activity of the defructosylation enzyme of the present invention originating from a plant belonging to the family Zingiberaceae or to determine a fructosylated peptide or protein, generated defructosyl peptides may be isolated and identified through HPLC or capillary electrophoresis. Alternatively, an appropriate carboxypeptidase may be reacted with the defructosyl peptide, to thereby detect or measure the generated amino acid residues. For example, when the fructosyl peptide having fructosylated valine at the N-terminus thereof and having an amino acid sequence represented by SEQ ID NO: 5 is reacted with carboxypeptidase, glutamic acid (Glu), proline (Pro), threonine (Thr), leucine (Leu), histidine (His), and valine (Val) are generated. Among these amino acid residues, Glu, Leu, and Val can be detected or determined by measuring the amount of NADH or NADPH produced through use of glutamate dehydrogenase, leucine dehydrogenase, and valine dehydrogenase, respectively. Glucosone produced concurrently with defructosyl peptide can be detected or determined by generating hydrogen peroxide through use of, among others, glucose oxidase and then measuring the produced hydrogen peroxide in a known peroxidase color-developing system. When the defructosylation enzyme employed in defructosylation reaction produces hydrogen peroxide, the produced hydrogen peroxide may be directly detected or determined through use of a peroxidase color-developing system.

No particular limitation is imposed on the peroxidase (POD) color-developing system. Suitable is a method in which a chromogen and POD are added to the reaction system so that the chromogen is oxidized thereby producing a color-developing substance, followed by measuring the substance. As the chromogen, there may be employed a combination of 4-aminoantipyrine and a phenol compound, a naphthol compound, or an aniline compound, a combination of MBTH (3-methyl-2-benzothiazolinone hydrazone) and an aniline compound, leucomethylene blue, or similar substances. Alternatively, a method as described in Japanese Patent No. 2516381 may be employed. Specifically, in the presence of POD, hydrogen peroxide is reacted with divalent cobalt ion, and the produced trivalent cobalt ion is treated with a trivalent-cobalt-ion-specific indicator such as TASBB (2-(2-thiazolylazo)-5-disulfobutylaminobenzoic acid trisodium salt), thereby producing a color-developing chelate compound, followed by measuring the chelate compound. The latter method provides measurement sensitivity 5 to 10 times that provided by the former method. As an alternative reagent for detecting hydrogen peroxide, TPM-PS (N,N,N',N',N",N"-hexa(3-sulfopropyl)-4,4',4"-triaminotriphenylmethane) (product of Dojindo Laboratories), which can be measured with high sensitivity, or a similar reagent may be employed.

According to the method of the present invention, a peptide or protein having a fructosyl valine residue at the N-terminus thereof such as HbA1c can be quantified with very high accuracy. Examples of test samples to be employed to quantify HbA1c include whole blood and erythrocyte.

EXAMPLES

The present invention will next be described in more detail by way of examples, which should not be construed as limiting the invention thereto.

Example 1

Preparation of defructosylation enzyme originating from a plant belonging to the family Zingiberaceae A Zingiber officinale rhizome was directly crushed by means of a juicer, and the product was left to stand. Thereafter, the product was subjected to centrifugal separation to remove solid substances, whereby a crude extract was obtained. A filter aid Celite 545 (trade name, product of Nacalai Tesque, Inc.) was added to the crude extract, followed by stirring, and the mixture was filtrated through use of a paper filter under suction. The filtrate was again subjected to centrifugation, thereby yielding an extract. The same amount of cold ethanol was added to the extract, to thereby form a precipitate. The precipitate was dissolved in a small amount of 20 mM phosphate buffer (pH 7.0), and the solution was added to a DEAE TOYOPEARL column (Product of Tosoh Corporation), whereby a fraction containing non-adsorbed substances was recovered. When necessary, the fraction was concentrated through ultrafiltration, and the filtrate served as a crude enzyme solution.

Example 2

Method of Defructosylating Fructosyl Peptide (i) A 100 mM phosphate buffer (pH 8.0) (100 µL), a 500 µM aqueous solution (40 µL) of the N-terminal-valine fructosylated peptide having an amino acid sequence represented by SEQ ID NO: 2 (f-VHL: products of Bioquest), purified water (20 µL), and the Zingiberaceae-plant-origin crude enzyme solution (40 µL) prepared in Example 1 were mixed together, and the mixture was caused to react for 16 hours at 37° C. The reaction mixture was subjected to ultrafiltration (molecular weight: 10,000), and the filtrate was collected (reaction mixture 1). The reaction mixture 1 was analyzed through use of a capillary electrophoresis apparatus CAPI-3200 (product of Otsuka Electronics Co., Ltd) (electrophoresis buffer: 150 mM phosphate buffer (pH 2.0), voltage: 15 kV, detection wavelength: 210 nm) in terms of peak position and peak area.

(ii) Control Test

As a control, purified water was added instead of the crude enzyme solution, and the resultant mixture was allowed to react under similar conditions, to thereby prepare a filtrate (control solution 1). The analysis results obtained from the control solution 1 were compared with those of the reaction mixture 1.

The fructosyl peptide employed in the enzyme reaction or control test had been mixed with corresponding non-fructosylated peptide. The presence or absence of the enzyme activity was determined through comparison of the two peaks.

Figure 2:
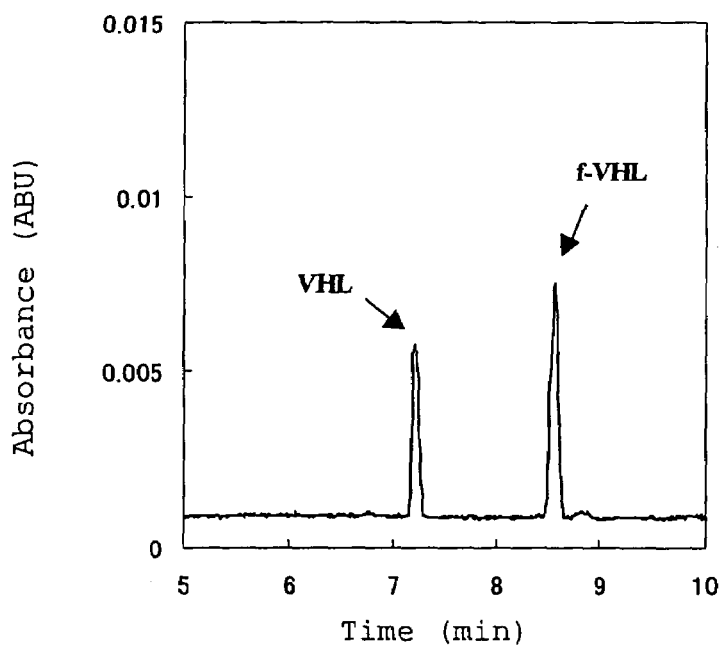
FIG. 2 shows the results of capillary electrophoresis obtained from the control solution 1 prepared by reacting purified water with fructosyl tripeptide (f-VHL).

FIG. 1 shows the results obtained from the reaction mixture 1, and FIG. 2 shows the results obtained from the control solution. Whereas FIG. 2 reveals a peak attributed to f-VHL (area: 32 mABU×sec) and a peak attributed to VHL (area: 22 mABU×sec), FIG. 1 reveals that the peak attributed to f-VHL does not exist and the peak attributed to VHL is increased (area: 32 mABU×sec).

These results substantiate that use of the enzyme originating from a plant belonging to the family Zingiberaceae is effective of defructosylating fructosyl peptides.

Example 3

The enzyme originating from a plant belonging to the family Zingiberaceae, an enzyme of the present invention, has the following physical and chemical characteristics.

a) Action and Substrate Specificity

Enzyme activity of the enzyme was measured by use of, as a substrate, each of a fructosyl amino acid residue (fructosyl valine) solution and solutions of fructosyl peptides (at least peptides having amino acid sequences represented by SEQ ID NOs: 1 to 5 were measured). The results indicate that the enzyme is effective on fructosyl valine and at least fructosyl peptides having amino acid sequences represented by SEQ ID NOs: 1 to 5.

b) Optimum pH

Figure 3:
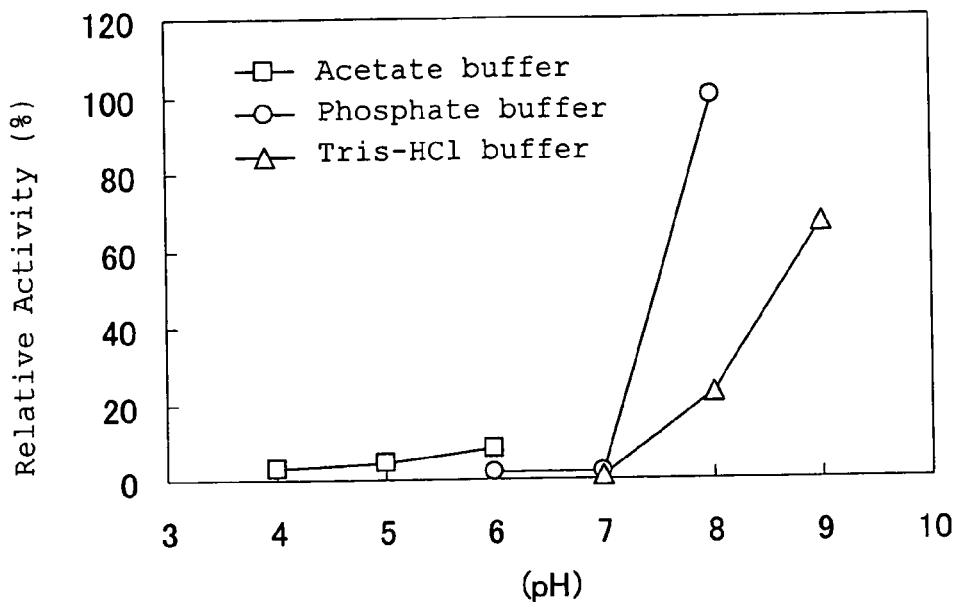
FIG. 3 shows relative activity of the Zingiberaceae-plant-origin enzyme at different pH.

Enzyme activity was measured at different pHs by producing glucosone through use of different buffers; i.e., 200 mM acetate buffer (pH 4.0 to 6.0), 200 mM phosphate buffer (pH 6.0 to 8.0), and 200 mM Tris-HCl buffer (pH 7.0 to 9.0) in accordance with the above-described method for measuring enzyme activity. The results are shown in FIG. 3. The enzyme of the present invention originating from a plant belonging to the family Zingiberaceae exhibits the highest enzyme activity at pH 8.0 (phosphate buffer) and at pH 9.0 (Tris-HCl buffer). Thus, the Zingiberaceae-plant-originating enzyme was determined to have an optimum pH of 8.0 to 9.0.

c) Stable pH Range

Figure 4:
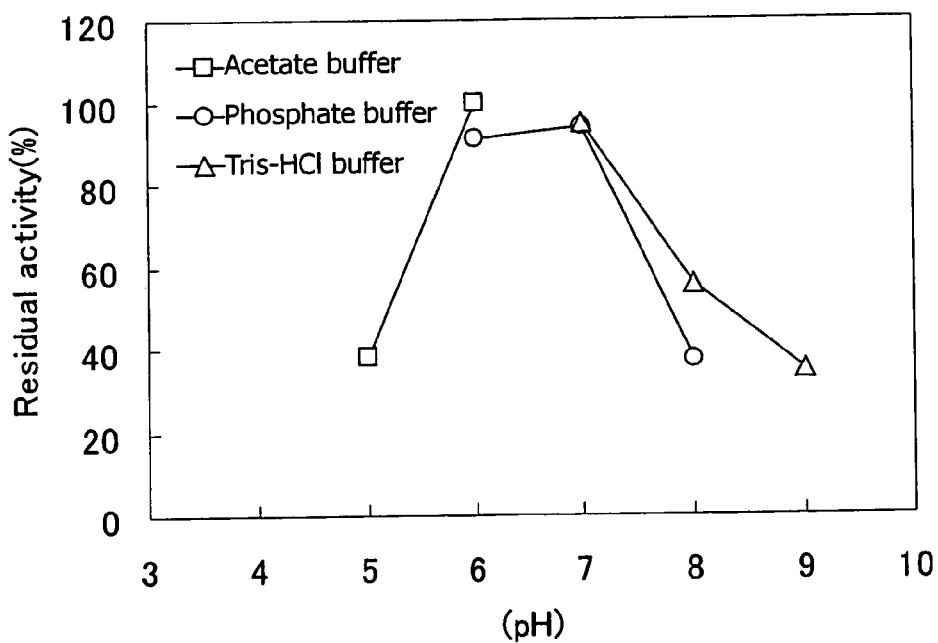
FIG. 4 shows stability of the Zingiberaceae-plant-origin enzyme at different pH.

The enzyme was measured in terms of residual enzyme activity after treatment for 15 minutes at 60° C. with 50M acetate buffer (pH 4.0 to 6.0), 50 mM phosphate buffer (pH 6.0 to 8.0), or 50 MM Tris-HCl buffer (pH 7.0 to 9.0). The results are shown in FIG. 4. The enzyme exhibits the highest residual activity at pH 6.0 to 7.0. Thus, the enzyme originating from a plant belonging to the family Zingiberaceae was found to be stable at a pH ranging from 6.0 to 7.0.

d) Km Value for Fructosyl Valyl Histidine

The Michaelis constant (Km) value of the enzyme for a substrate fructosyl valyl histidine was determined by measuring enzyme activity through use of fructosyl valyl histidine solutions having different concentrations in accordance with the above-described method for measuring enzyme activity and using Lineweaver-Burk's plots. The results indicate that the Km value of the enzyme for fructosyl valyl histidine: 1.2 mM.

e) Optimum Temperature Range

Figure 5:
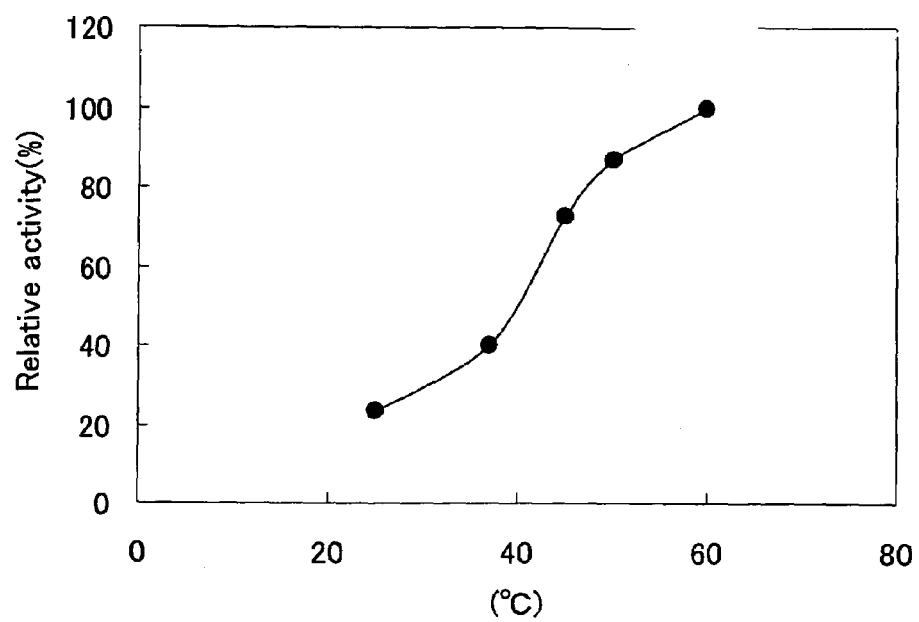
FIG. 5 shows relative activity of the Zingiberaceae-plant-origin enzyme at different temperatures.

Enzyme activity of the enzyme was measured at different reaction temperatures between 0° C. and 60° C. in accordance with the above-described method for measuring enzyme activity. The results are shown in FIG. 5. In this temperature range, enzyme activity increased in accordance with the increase in reaction temperature, and decrease in activity was not observed, indicating that the enzyme originating from a plant belonging to the family Zingiberaceae has an optimum temperature range of 60° C. or higher.

f) Temperature Stability

Figure 6:
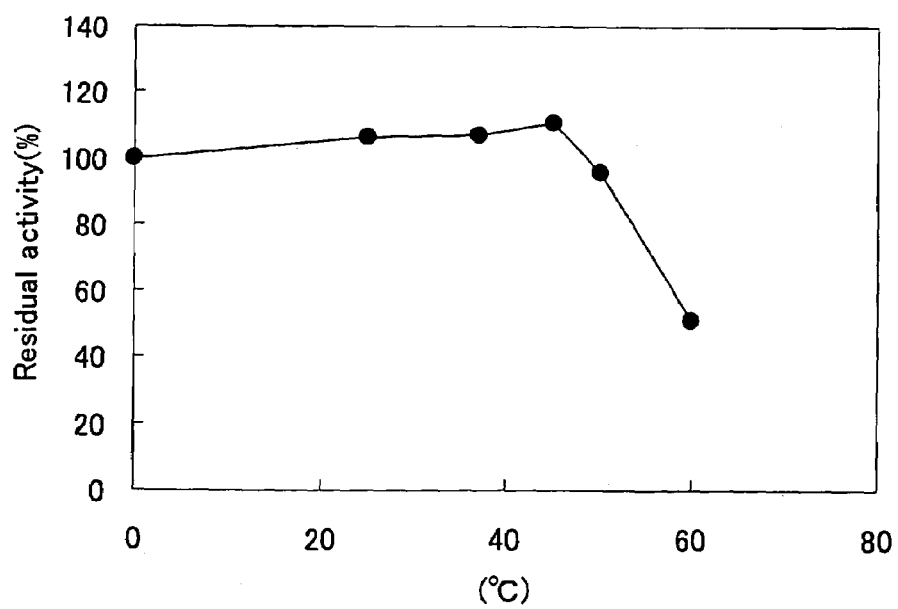
FIG. 6 shows temperature stability of the Zingiberaceae-plant-origin enzyme.

The residual activity of enzyme was measured after the enzyme was treated with 50 mM phosphate buffer (pH 8.0) for 15 minutes at different temperatures. The results are shown in FIG. 6. After treatment for 15 minutes at 50° C., 80% or more of the enzyme activity remained. The enzyme was found to be stable at a temperature up to around 50° C.

g) Molecular Weight

The crude enzyme solution prepared in Example 1 was subjected to gel filtration chromatography employing a Sephacryl S-200 (Amersham Bioscience K.K.) column. 20 mM Phosphate buffer (pH 6.0) containing 150 mM NaCl was used as an eluent, and calibration for the Sephacryl S-200 column with respect to molecular weight was performed through use of a Gel Filtration Calibration Kit (Amersham Bioscience K.K.). Thus, the molecular weight of the enzyme originating from Zingiber officinale was calculated to be around 27 kDa. The solution of the enzyme having a molecular weight of around 27 kDa was employed in the studies described below. In this connection, the enzyme reaction for producing glucosone referred to in the above-described method for measuring activity employed a 1.6-unit/mL enzyme solution, and the reaction was performed for 60 minutes at 37° C.

Example 4

Figure 7:
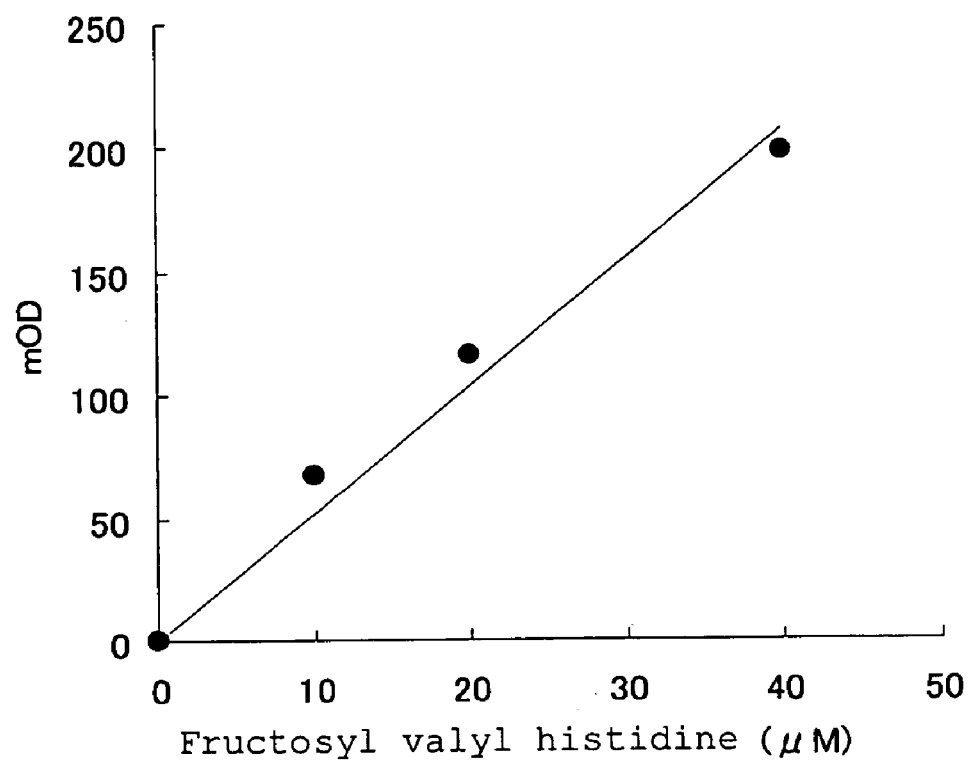
FIG. 7 shows the results of measurement of fructosyl peptide through use of the plant-origin defructosylation enzyme of the present invention.

Method for Measuring Fructosyl Peptide 200 mM Phosphate buffer (pH 8.0) (150 μL), purified water (360 μL), and each of aqueous fructosyl valyl histidine solutions (60 μL) having different concentrations were mixed together so that the final fructosyl valyl histidine concentrations after reaction fell between 0 and 40 μM. The reaction was mixed with a solution of the enzyme originating from *Zingiber officinale* (1.6 u/mL) (30 μL), and the resultant mixture was allowed to react for 16 hours at 37° C. Subsequently, a mixture which had been prepared in advance by mixing 200 mM acetate buffer (pH 6.0) (750 μL), 4000-u/mL glucose oxidase (Toyobo Co., Ltd.) (450 μL), 0.15% 4-aminoantipyrine (300 μL), 0.3% TOOS (Dojindo Laboratories) (300 μL), 500-u/mL peroxidase (Toyobo Co., Ltd.: Type III) (300 μL), and 1% sodium azide (300 μL) was added to the reaction mixture, and the resultant mixture was treated for 10 minutes at 37° C., followed by measuring absorbance at 550 nm (FIG. 7). The absorbance was found to increase in accordance with the increase in concentration of fructosyl valyl histidine, confirming that glucosone was produced from the fructosyl peptide through the action of the enzyme of the present invention originating from *Zingiber officinale* and that the method of the present Example enables measurement of fructosyl peptide.

Example 5

To a 50 mM phosphate buffer (pH 8.0) containing 0.5 mM DA-64 (product of Wako Pure Chemical Industries, Ltd.), 200-u/mL POD, 0.1% sodium azide, and 1mM fructosyl valine or fructosyl peptide (SEQ ID NOs: 1 to 5) (all being final concentrations), a *Zingiber officinale*-originating enzyme solution was added in an amount of 0.3 u/mL (final concentration), and the mixture was treated for 30 minutes at 50° C. Absorbance at 700 nm was measured by employment of purified water as a control. Color development of DA-64 was observed (Table 1). Thus, hydrogen peroxide was confirmed to be produced.

TABLE 1

|  | Absorbance at 700 nm (mAbs) |
| --- | --- |
| Fructosyl valine | 512 |
| f-VH | 735 |
| f-VHL | 570 |
| f-VHLT | 558 |
| f-VHLTP | 198 |
| f-VHLTPE | 223 |

The invention claimed is:

1. A method of defructosylating a fructosylated peptide or protein, comprising reacting the peptide or protein with an enzyme that is extracted from a plant of the genus Zingiber and exhibits defructosylation action.

2. The defructosylation method according to claim 1, wherein the fructosylated peptide comprises the amino acid sequence of any of SEQ ID NOs: 1 to 5.

3. The defructosylation method according to claim 1 or claim 2, wherein the fructosylated protein is hemoglobin A1 c.

4. An enzyme that exhibits defructosylation action on a fructosylated peptide or protein and is extracted from a plant of the genus *Zingiber*.

5. The enzyme according to claim 4, wherein the enzyme has the following physical and chemical characteristics a) to h):

a) Action: in the presence of oxygen, acting on a fructosyl valine or fructosyl peptide wherein the fructosyl peptides may be selected from peptides comprising the amino acid sequences of SEQ ID NOs: 1 to 5, and catalyzing at least a reaction which produces corresponding valine or non-fructosyl peptide, glucosone, and hydrogen peroxide;

b) Optimum pH: 8.0 to 9.0;

c) Range of stable pH: pH 6.0 to 7.0;

d) Km value for fructosyl valyl histidine: 1.2 mM;

e) Range of optimum temperature: 60° C. or more;

f) Temperature stability: 80% or more of the enzyme activity remains after heat-treatment for 15 minutes at 50° C.; and g) Molecular weight: approximately 27 kDa by gel filtration.

6. A method for measuring a fructosylated peptide or protein, comprising measuring at least one reaction product produced through the defructosylation method according to claim 1 or claim 2.

7. The method for measuring a fructosylated-peptide or protein according to claim 6, wherein the reaction product produced through the defructosylation method is hydrogen peroxide, glucosone, or a defructosyl peptide.

* * * * *

SEQUENCE LISTING

```
<160> NUMBER OF SEQ ID NOS: 5

<210> SEQ ID NO 1
<211> LENGTH: 2
<212> TYPE: PRT
<213> ORGANISM: Artificial
<220> FEATURE:
<223> OTHER INFORMATION: Synthetic Peptide

<400> SEQUENCE: 1

Val His
1

<210> SEQ ID NO 2
<211> LENGTH: 3
<212> TYPE: PRT
<213> ORGANISM: Artificial
<220> FEATURE:
<223> OTHER INFORMATION: Synthetic Peptide

<400> SEQUENCE: 2

Val His Leu
1

<210> SEQ ID NO 3
<211> LENGTH: 4
<212> TYPE: PRT
<213> ORGANISM: Artificial
<220> FEATURE:
<223> OTHER INFORMATION: Synthetic Peptide
```

```
<400> SEQUENCE: 3

Val His Leu Thr
1

<210> SEQ ID NO 4
<211> LENGTH: 5
<212> TYPE: PRT
<213> ORGANISM: Artificial
<220> FEATURE:
<223> OTHER INFORMATION: Synthetic Peptide

<400> SEQUENCE: 4

Val His Leu Thr Pro
1               5

<210> SEQ ID NO 5
<211> LENGTH: 6
<212> TYPE: PRT
<213> ORGANISM: Artificial
<220> FEATURE:
<223> OTHER INFORMATION: Synthetic Peptide

<400> SEQUENCE: 5

Val His Leu Thr Pro Glu
1               5
```